United States Patent [19]
Kunst

[11] Patent Number: 5,836,317
[45] Date of Patent: Nov. 17, 1998

[54] TRANSCUTANEOUS NON-BLOODY DETERMINATION OF THE CONCENTRATION OF SUBSTANCES IN THE BLOOD

[76] Inventor: Hermann Kunst, Treuenbrietzener Strasse 20, Berlin D-13439, Germany

[21] Appl. No.: 737,585
[22] PCT Filed: May 19, 1995
[86] PCT No.: PCT/DE95/00664
  § 371 Date: Jan. 17, 1997
  § 102(e) Date: Jan. 17, 1997
[87] PCT Pub. No.: WO95/31928
  PCT Pub. Date: Nov. 30, 1995

[30] Foreign Application Priority Data

May 20, 1994 [DE] Germany .......................... 44 17 849.2

[51] Int. Cl.⁶ .................................................. A61B 19/00
[52] U.S. Cl. ........................... 128/898; 600/322; 600/316
[58] Field of Search .................................. 128/898, 633, 128/637, 632, 653.1–653.3, 664, 687, 691; 436/95, 811, 815, 901; 600/310, 309, 322, 368, 410, 473, 500, 504, 316

[56] References Cited

U.S. PATENT DOCUMENTS

| | | | |
|---|---|---|---|
| 4,655,225 | 4/1987 | Dahne et al. . | |
| 4,882,492 | 11/1989 | Schlager ................................... | 128/637 |
| 4,883,953 | 11/1989 | Koashi et al. . | |
| 4,975,581 | 12/1990 | Robinson et al. . | |
| 5,101,825 | 4/1992 | Gravenstein et al. . | |
| 5,137,023 | 8/1992 | Mendelson et al. . | |
| 5,139,023 | 8/1992 | Stanley et al. ........................... | 128/637 |
| 5,178,142 | 1/1993 | Harjunmaa et al. . | |
| 5,183,042 | 2/1993 | Harjunmaa et al. . | |
| 5,285,782 | 2/1994 | Prosser . | |
| 5,313,941 | 5/1994 | Braig et al. . | |
| 5,372,135 | 12/1994 | Mendelson et al. . | |
| 5,425,868 | 6/1995 | Pedersen .................................. | 204/408 |
| 5,526,808 | 6/1996 | Kaminsky ................................ | 128/632 |
| 5,598,842 | 2/1997 | Ishihara et al. .......................... | 128/637 |

FOREIGN PATENT DOCUMENTS

| | | | |
|---|---|---|---|
| 0404562 | 12/1990 | European Pat. Off. . | |
| 4128458 | 3/1993 | Germany . | |
| 004242083 | 6/1994 | Germany ............................... | 128/637 |
| 004242232 | 6/1994 | Germany ............................... | 128/637 |
| 9115991 | 10/1991 | WIPO . | |
| 9312712 | 7/1993 | WIPO . | |

OTHER PUBLICATIONS

The International Search Report and Annex in German and English.
The International Preliminary Examination Report in German and English.
Harrison et al. "Spectrophotometric measurments of haemoglobin saturation and concentration in skin during the tuberculin reaction in normal human subjects." Clin Phys Physiol Meas 13(4): 349–364, Nov. 1992.
Schlager, K.G. "Transcutaneous Analyte measuring methods (TAMM Phase 2)." Quarterly progress report No. 7, Biotronics Technologies, Inc., 5–22, Oct. 1993.
Schlager et al. "TAMM–a reflective, near infrared blood chemistry analyzer." SPIE 2386:174–184, Feb. 1995.

*Primary Examiner*—Mickey Yu
*Assistant Examiner*—Kelly O'Hara
*Attorney, Agent, or Firm*—Greenblum & Bernstein P.L.C.

[57] ABSTRACT

Methods for transcutaneous and non-bloody in vivo determination of an analyte in blood which includes spectroscopically generating at least one first signal corresponding to at least one analyte quantity in a region of a body and at least one second signal corresponding to at least one water quantity in the region of the body, determining the at least one analyte quantity based on the at least one first signal and the at least one water quantity based on the at least one second signal, calculating a concentration of the analyte in water by forming a ratio of an analyte value calculated on the basis of the at least one analyte quantity and a water value calculated on the basis of the at least one water quantity and calculating a concentration of the analyte in blood based on the ratio of the analyte value and the water value.

20 Claims, 3 Drawing Sheets

TRANSCUTANEOUS NON-BLOODY DETERMINATION OF THE CONCENTRATION OF SUBSTANCES IN THE BLOOD

BACKGROUND OF THE INVENTION

1. Field of the Invention

The invention relates to a process for transcutaneous and non-bloody in vivo determination of an analyte in blood.

2. Discussion of the Background

The number of persons suffering from diabetes, for example, particularly in highly industrialized countries, is extraordinarily high and is on the rise. The most recent estimates assume that there are 4 million people with this disease in the Federal Republic of Germany.

The treatment of this metabolic disease requires constant control and measurement of blood sugar content. Deviations from the norm lead to known latent injuries, whose result is, for example, blindness or amputation.

The currently available measurement methods are invasive, i.e., they require the withdrawal of blood and hence, injury to the patient. In comparison, a non-invasive, i.e., injury-free blood sugar measurement has a number of advantages which cannot be achieved with the known processes and methods.

A non-invasive procedure comparatively reduces the strain upon the diabetic patient, improves the adjustment precision of the blood sugar level for the prevention of latent injuries, in particular through the possibility of continuous registering of the blood sugar concentration, permits the testing of dynamic metabolic processes and the development of an artificial pancreas by designing a governing circuit for a blood sugar-insulin pump.

Until now, various methods have been considered which utilize chemical, biological, and physical processes or principles.

U.S. Pat. No. 5,137,023 discloses an embodiment in which an at first undetermined glucose quantity is measured by determining the absorption difference at a particular wavelength. The association of this measurement value with a corresponding glucose concentration in the blood, though, must still be carried out with a standard measurement for each patient, wherein the standard test sample naturally has to be withdrawn in a bloody manner. In this connection, it is assumed that the conditions at the measurement location or in the measurement area do not change. Temperature changes and changes in the sample thickness (e.g., fingertip or earlobe) can lead to deviations from the standard and thus can increase measurement error.

Changes in the measurement area, which likewise lead to increased measurement error, can be attributed to external physiological influences on the patient, such as stress, anger, and athletic activity. This is partially combated with correction values that take these influences (sample thickness, temperature measurement) into account.

With the known process, the total glucose content in the measurement area (blood, skin, tissue, bone) of a region of the body is additionally measured. Dynamic changes of the concentration in the blood can only be determined in terms of their direction.

U.S. Pat. No. 5,101,825 describes a process in which a quantity of a substance of interest is measured in parallel to the measurement of a reference volume.

Having the disadvantages mentioned, the precision of the known process leads to the fact that despite considerable uses in the research field, no possibility has been produced for completely non-invasive, in vivo measurement of blood sugar. Thus, for example, a regulation of the insulin that can be supplied with a pump as a function of the measured glucose concentration cannot be carried out precisely enough.

SUMMARY OF THE INVENTION

It is therefore the object of the invention to produce a possibility for in vivo measurement of the concentration of substances such as glucose, lactate, blood sugar, cholesterol, alcohol, drugs, or the like in the patient's blood in a completely non-bloody manner and with increased precision.

According to the invention, this object is attained by spectroscopically generating at least one first signal corresponding to at least one analyte quantity in a region of a body and at least one second signal corresponding to at least one water quantity in the region of the body; determining the at least one analyte quantity based on the at least one first signal and the at least one water quantity based on the at least one second signal; calculating a concentration of the analyte in water by forming a ratio of a value related to the at least one analyte quantity and a value related to the at least one water quantity; and calculating a concentration of the analyte in blood based on the ratio. Advantageous embodiments and improvements ensue from employment of the features contained in the dependent claims.

DETAILED DESCRIPTION

Figure 1:
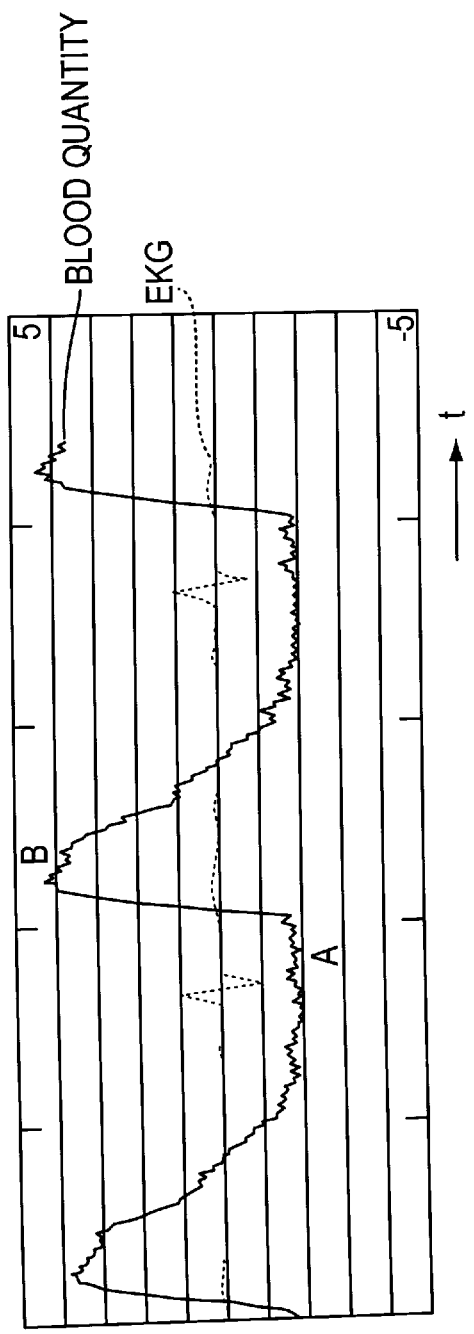
FIG. 1 shows the circulatory change in the index finger in relation to the electrocardiogram (EKG). The molecules are measured at the maximal (point B) and minimal (point A) blood content.

With the aid of signals as to the quantity of a substance and the quantity of water that are present in a given tissue region, measured using known spectroscopic methods, the concentration of the substance in the water is determined through the formation of the ratio of the measured signals for the substance quantity and water quantity and the concentration value in the blood is calculated from this ratio.

As a result, the determination of the water content and glucose content is very simple, wherein the determination of the absolute values for both components is not required. This would again require a standard measurement that is bloody. With the process according to the invention, it is sufficient to determine the ratio of glucose or another contained substance to water. One molecule determines the specific properties, and the number of the respective molecules determines the intensity of the action of this substance. The number of the water molecules determined is thus used as a reference value for determining the concentration.

It is advantageous to measure the signal values for the quantity of the substance and the water quantity at the time of the systole and the diastole and to bring into play the difference between the two measurement values to form a ratio. Since the measurement is carried out in an arbitrary tissue region, the subtraction of the systolic and diastolic signal values can rule out a possible influence of the measurement value by means of the surrounding tissue region. The embodiment is therefore preferable because it permits the determination of the exact values alone in water. This process according to the invention can therefore be carried out at a point on the body at which there is a change in blood quantity over time. This is the case, e.g., at the fingertip, the earlobe, or in surface veins.

The signal determination is preferably carried out in a characteristic wavelength range of the spectrum. The procedure is carried out so that the characteristic absorption frequencies of the substance are first determined empirically, and then a signal is generated at these frequencies by means of a spectroscopic method. This is also true for the substance (e.g., glucose) and water.

However, substance-in-water reference spectra can also be determined and compared. To that end, substance/water spectra can be recorded at different concentrations and then compared to the spectra determined.

This method, which works according to the principle of pattern recognition, has the advantage that the concentration of the substance to be determined can be ascertained with a high degree of precision, even when there is noise and in the presence of additional substances.

According to the invention, first the concentration of the substance is determined with a reference molecule. Water is chosen since it makes up a high, relatively stable percentage of 85%±2.4% in the blood. To determine the blood value, the water value is then converted to 100%. It has turned out that the error that occurs in this connection can be ignored.

The course of the process is explained in detail below in the example of glucose.

FIG. 1 shows the circulatory change in the index finger in relation to the electrocardiogram (EKG). The molecules are measured at the maximal (point B) and minimal (point A) blood content.

Figure 2:
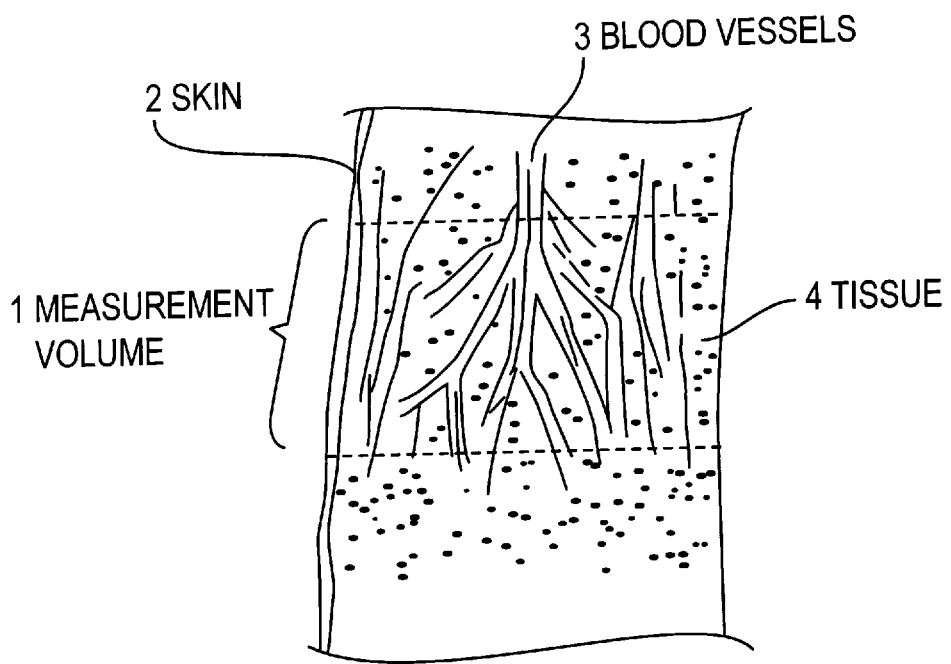
FIG. 2 shows the conditions in the measurement volume. In it, 1) is measurement volume, 2) is skin, 3) is blood vessels, and 4) is tissue.

FIG. 2 shows the conditions in the measurement volume. In it, 1) is measurement volume, 2) is skin, 3) is blood vessels, and 4) is tissue.

The following associations are true:
NB,GL(A) number of glucose molecules in the blood in the diastole;
NB,GL(B) number of glucose molecules in the blood in the systole;
NB,W(A) number of water molecules in the blood in the diastole;
NB,W(B) number of water molecules in the blood in the systole;
NG,GL(A) number of glucose molecules in the tissue in the diastole;
NG,GL(B) number of glucose molecules in the tissue in the systole;
NG,W(A) number of water molecules in the tissue in the diastole;
NG,W(B) number of water molecules in the tissue in the systole;

The glucose concentration can be determined with $$C = KB^* NB,GL(A)/NB,W(A) = KB^* NB,GL(B)/NB,W(B) \quad (1)$$

since the concentration in the maximum and minimum of the blood content (systole, diastole) is constant, wherein KB is a correction factor which takes into account the percentage portion of water in the blood.

The number of glucose molecules in the measurement volume at time A follows from this, with $$N,GL(A) = NB,GL(A) + NG,GL(A) \quad (2)$$

and the number of water molecules with $$N,W(A) = NB,W(A) + NG,W(A). \quad (3)$$

The values at time B are determined analogously:

$$N,GL(B) = NB,GL(B) + NG,GL(B) \quad (4)$$

as the total number of glucose molecules and $$N,W(B) = NB,W(B) + NG,W(B) \quad (5)$$

as the total number of water molecules.

The number of respective molecules remains constant in the tissue independent of the time A and B. In the blood, though, it changes between these two states and with equations (1) and (2), $$N,GL(A) - N,GL(B) = NB,GL(A) - NB,GL(B) \quad (6)$$

and at the same time, analogously from equations (3) and (5), $$N,W(A) - N,W(B) = NB,W(A) - NB,W(B). \quad (7)$$

By inserting equation (1) into equation (6), $$N,GL(A) - N,GL(B) = c/KB^*(NB,W(A) - NB,W(B)) \quad (8)$$

and the division by equation (7) yields $$(N,GL(A) - N,GL(B))/(N,W(A) - N,W(B)) = C/KB$$

or $$C = KB^*(N,GL(A) - N,GL(B))/(N,W(A) - N,W(B)). \quad (9)$$

As a result, a determination of the glucose concentration alone is possible with maximally four measurements, and the influence of disturbance variables, such as possible changes in the tissue, is ruled out.

If the measurement values of the glucose molecules and water molecules of interest are selectively measured correspondingly for an evaluation according to equation (9), various measurement processes can be used. Thus infrared spectroscopy, Raman spectroscopy, or nuclear magnetic resonance spectroscopy can be used. The selective measurement of the molecules, e.g. in the infrared range, is connected with some expenditure because of the wide, overlapping absorption bands.

The molecules can be recognized in nuclear magnetic resonance spectroscopy because of the chemical dislocation of the nucleus bonded in one molecule. The area below the resonance curve, however, is proportional to the number of nuclei or molecules and the measurement values that can be processed in accordance with equation (9) can be attributed to the measurement of the area differences.

Figure 3:
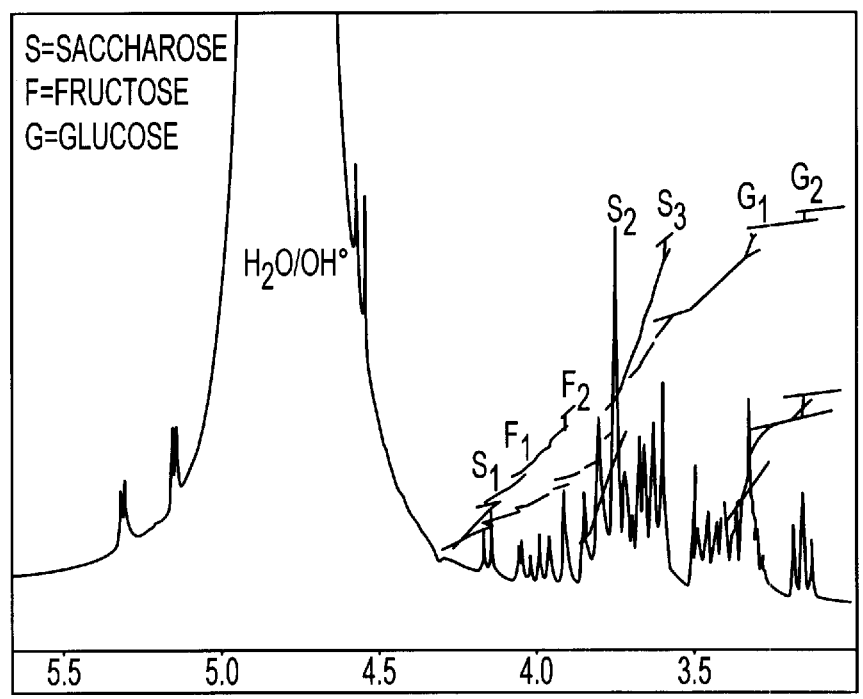
FIG. 3 shows the 1H-NMR spectra of a sugar mixture in water.

FIG. 3 shows the 1H-NMR spectra of a sugar mixture in water. The lines of glucose denoted with G1 and G2 differ considerably from the others as does the water line. The sensitivity of nuclear magnetic resonance spectroscopy can be increased multifold by means of optical pumps with a light source having a suitable wavelength. In comparison, methods that are known for the same purpose from measurement value processing, such as digital filtering, Fourier analysis, correlation analysis, and multiple addition are used to improve the signal/noise ratio. The sensitivity of the concentration determination is positively influenced chiefly by means of the unaccompanied detection through measurement technology and the processing of differences.

A connection with the EKG signal or another composite signal proportional to the blood volume has an advantageous effect upon the further increase of the sensitivity. However, a number of measurement processes can also be used in combination.

I claim:

1. A method for transcutaneous and non-bloody in vivo determination of an analyte in blood, comprising:

(a) spectroscopically generating at least one first signal corresponding to at least one analyte quantity in a region of a body and at least one second signal corresponding to at least one water quantity in the region of the body;

(b) determining the at least one analyte quantity based on the at least one first signal and determining the at least one water quantity based on the at least one second signal;

(c) calculating a concentration of the analyte in water by forming a ratio of a value related to the at least one analyte quantity and a value related to the at least one water quantity; and (d) calculating a concentration of the analyte in blood based on the ratio.

2. The method according to claim 1, wherein a first analyte quantity is determined for a time of a diastole, a second analyte quantity is determined for a time of a systole, a first water quantity is determined for a time of a diastole, and a second water quantity is determined for a time of a systole.

3. The method according to claim 2, wherein the value related to the at least one analyte quantity is determined by forming the difference of the first analyte quantity and the second analyte quantity and the value related to the at least one water quantity is determined by forming the difference of the first water quantity and the second water quantity.

4. The method according to claim 3, wherein the concentration of the analyte in blood is determined by multiplying the ratio by a correction factor which takes into account a percentage portion of water in the blood.

5. The method according to claim 1, wherein the concentration of the analyte in blood is calculated by multiplying the ratio by a correction factor which takes into account a percentage portion of water in the blood.

6. The method according to claim 1, wherein the analyte is selected from the group consisting of glucose, lactate, blood sugar, cholesterol, alcohol and drugs.

7. The method according to claim 1, wherein the at least one first signal and the at least one second signal are generated at characteristic absorption frequencies of the analyte and water.

8. The method according to claim 1, wherein the at least one analyte quantity and at the least one water quantity are determined by pattern recognition.

9. The method according to claim 1, wherein the at least one first signal and the at least one second signal are generated by infra-red spectroscopy.

10. The method according to claim 1, wherein the at least one first signal and the at least one second signal are generated by Raman spectroscopy.

11. The method according to claim 1, wherein the at least one first signal and the at least one second signal are generated by nuclear magnetic resonance spectroscopy.

12. The method according to claim 1, wherein the region of the body is a region with a pulsing quantity of blood.

13. The method according to claim 1, wherein the region of the body is a fingertip, an earlobe or a vein.

14. A method for transcutaneous and non-bloody in vivo determination of an analyte in blood, comprising:

(a) spectroscopically generating a signal corresponding to an analyte quantity at diastole and a signal corresponding to an analyte quantity at systole in a region of a body;

(b) determining the analyte quantity at diastole based on the signal corresponding to the analyte quantity at diastole and determining the analyte quantity at systole based on the signal corresponding to the analyte quantity at systole;

(c) spectroscopically generating a signal corresponding to a water quantity at diastole and a signal corresponding to a water quantity at systole in a region of a body;

(d) determining the water quantity at diastole based on the signal corresponding to the water quantity at diastole and determining the water quantity at systole based on the signal corresponding to the water quantity at systole;

(e) calculating a ratio of a difference of the analyte quantity at diastole and the analyte quantity at systole and a difference of the water quantity at diastole and the water quantity at systole; and (f) multiplying the ratio by a correction factor for percentage portion of water in blood.

15. The method according to claim 14, wherein the analyte is selected from the group consisting of glucose, lactate, blood sugar, cholesterol, alcohol and drugs.

16. The method according to claim 14, wherein the signals are generated at characteristic absorption frequencies of the analyte and water.

17. The method according to claim 14, wherein the analyte quantities and the water quantities are determined by pattern recognition.

18. The method according to claim 14, wherein the signals are generated by infra-red spectroscopy.

19. The method according to claim 14, wherein the signals are generated by Raman spectroscopy.

20. The method according to claim 14, wherein the signals are generated by nuclear magnetic resonance spectroscopy.

* * * * *